United States Patent [19]

Buck et al.

[11] Patent Number: 5,518,914
[45] Date of Patent: May 21, 1996

[54] GROWTH MEDIUM CONTAINING A COMPLEX OF PREALBUMIN, A RETINOID AND RETINOL-BINDING PROTEIN USED TO ENHANCE B CELL GROWTH

[75] Inventors: Jochen Buck; Urlich Hammerling, both of New York, N.Y.

[73] Assignee: Sloan-Kettering Institute for Cancer Research, New York, N.Y.

[21] Appl. No.: 456,644

[22] Filed: Jun. 2, 1995

Related U.S. Application Data

[63] Continuation of Ser. No. 283,993, Aug. 1, 1994, abandoned, which is a continuation of Ser. No. 7,807, Jan. 22, 1993, abandoned, which is a continuation of Ser. No. 387,013, Jul. 28, 1989, abandoned, which is a continuation-in-part of Ser. No. 206,569, Jun. 14, 1988, abandoned.

[51] Int. Cl.$^6$ ............................... C12N 5/00; C12P 21/04
[52] U.S. Cl. .................... 435/240.3; 435/240.2; 435/70.1; 435/70.3; 435/70.4; 530/399; 530/837; 530/838
[58] Field of Search .............................. 435/70.1, 70.2, 435/70.3, 70.4, 72.2, 240.2, 240.25, 240.26, 240.27, 240.3, 240.31, 100, 104, 108; 530/399, 402, 405, 837, 838

[56] References Cited

PUBLICATIONS

Ambrus et al., "Identification of a cDNA for a Human High–Molecular–Weight B–cell Growth Factor", *Proc. Natl. Acad. Sci. USA* 90:6330–6334, Jul. 1993.

Buck et al., "Differences in the Action and Metabolism Between Retinol and Retinoic Acid in B Lymphocytes," *J. Cell Biology* 115(3):851–859.

Goodman, D. S., "Plasma Retinol–Binding Protein," in *The Reintoids*, vol. 2, Academic Press, pp. 41–88.

Buck et al., "Purification and Biochemical Characterization of a Human Autocrine Growth Factor Produced by Epstein–Barr Virus Transformed B Cells", Journal of Immunology, v. 138, 2923–2928, May 1, 1987.

Ambrus et al. (A), "Human B Rymphoma cell line producing B cell growth factor", Journal of Clinical Investigation, v. 75, 732–739, 1985.

Ambrus et al. (B), "Purification to homogeneieth of a high molecular weight human B cell growth factors", J. Exp. Medicine, v. 162, 1319–1335, 1985.

Campbell, Laboratory Techniques: Monoclonal Antibody Technology, pp. 104 . 105, 1984.

*Primary Examiner*—Michael G. Withyshyn
*Assistant Examiner*—Kristin Kay Larson
*Attorney, Agent, or Firm*—John P. White

[57] ABSTRACT

This invention provides a complex consisting essentially of prealbumin, retinol-binding protein, and a retinoid which binds to retinol-binding protein, wherein the concentration of retinoid in the complex is from about $2\times10^{-5}$M to about $10^{-10}$M and the concentration of prealbumin and retinol-binding protein is sufficient to maintain the retinoid concentration from about $2\times10^{-5}$M to about $10^{-10}$M. This invention also provides a composition for enhancing the growth of human B cells in culture which comprises an amount of the complex of this invention effective to enhance the growth of human B cells and a nutrient medium. This invention further provides a method of enhancing growth of human B cells in culture comprising growing the cells in culture in a growth medium containing a concentration of the complex effective to enhance growth of the cells. This invention also provides a synthetic growth medium for culturing animal cells comprising the complex of this invention at a concentration effective to enhance cell growth. This invention also provides a method of preventing the growth of human tumor cells containing growth factor which comprises removing the growth factor from the human tumor cells.

11 Claims, 8 Drawing Sheets

FIGURE 1

```
              1                                    5
aBGF              Gly - Ser - Val - Gly - Ala - Gly - Glu -
Human Prealbumin  ----- Pro --Thr------Thr------------------

10
aBGF              Pro - Lys - Cys - Pro - Leu - Met - Val -
Human Prealbumin  Ser--------------------------------------

15                                   20
aBGF              Lys - Val - Leu - Asp - Ala - Val - Arg -
Human Prealbumin  -----------------------------------------

25
aBGF              Gly - Ser - Pro - Ala - Ala - Asn - Val
Human Prealbumin  -------------------------Ile-------------
```

GROWTH MEDIUM CONTAINING A COMPLEX OF PREALBUMIN, A RETINOID AND RETINOL-BINDING PROTEIN USED TO ENHANCE B CELL GROWTH

This invention was made with government support under Grant Number IM-480 from the American Cancer Society. Accordingly, the U.S. Government has certain rights in the invention.

This application is a continuation of 08/283,993 filed Aug. 1, 1994, now abandoned, which is a continuation of 08/007,807 filed Jan. 22, 1993, now abandoned, which is a continuation of 07/387,013 filed Jul. 28, 1989, now abandoned, which is a continuation-in-pan of 07/206,569 filed Jun. 14, 1988, now abandoned.

BACKGROUND OF THE INVENTION

Throughout this application, various publications are referenced by arabic numerals within parentheses. Full citation for these publications may be found at the end of the specification immediately preceding the claims. The disclosures of those publications in their entireties are hereby incorporated by reference into this application in order to more fully describe the state of the art as known to those skilled therein as of the date of the invention described and claimed.

Autocrine growth factors—factors produced by the target cells themselves—were first demonstrated for certain fibroblastic tumors in 1978 (1). Since then, autocrine growth factors have been described for several other tumors (2–5), and it has been recognized that normal cell such as activated T cells produce autocrine growth factors (6).

Blazer et al. (7) and Gordon et al. (8) reported that lymphoblastoid cell lines, (LCL) created by transformation with Epstein-Barr virus (EBV), make autocrine growth factors. The factors produced by one LCL stimulate growth of other LCL as well as of normal tonsillar B lymphocytes (9).

Buck et al. (10) described experiments to purify and characterize an autocrine growth factor produced by an EBV-transformed cell line. It was believed that the material was purified to apparent homogeneity and had no interleukin 1 activity.

Upon further study, the present inventors determined that the sequence of the protein was highly homologous to human prealbumin and that in fact bovine prealbumin had been isolated from fetal calf serum. It was also noted that the purified protein was not nearly as effective as a crude preparation, indicating the existence of a cofactor which was lost in later purification steps.

This cofactor was found to be a lipid, and through chromatography and other analysis it has been determined that the lipid is comprised of all-trans-retinol, commonly known as vitamin A. It has also been recognized that a second protein, retinol-binding protein, is contained in the growth factor.

Whereas neither prealbumin, retinol-binding protein or all-trans-retinol alone showed significant growth-promoting activity, the combination of the three did. This purified mixture possesses advantages over crude fetal calf serum because the former does not contain unknown components, is free from viruses and other hormones and growth factors and does not have the problem of impure antibodies containing calf serum for propagation of human or animal cell lines in cell culture.

The present invention, therefore, concerns the combination of prealbumin, retinol-binding protein and all-trans-retinol or other retinoids.

SUMMARY OF THE INVENTION

This invention provides a complex consisting essentially of prealbumin, retinol-binding protein, and a retinoid which binds to retinol-binding protein, wherein the concentration of retinoid in the complex is from about $2\times10^{-5}$M to about $10^{-10}$M and the concentration of prealbumin and retinol-binding protein is sufficient to maintain the retinoid concentration from about $2\times10^{-5}$M to about $10^{-5}$M.

This invention also provides a complex consisting essentially of retinol-binding protein and a retinoid which binds to retinol-binding protein, wherein the concentration of retinoid in the complex is from about $2\times10^{-5}$M to about $10^{-10}$M and the concentration of retinol-binding protein is sufficient to maintain the retinoid concentration from about $2\times10^{-5}$M to about $10^{-10}$M.

This invention also provides a composition for enhancing the growth of human B cells in culture which comprises an amount of the complex of this invention effective to enhance the growth of human B cells and a nutrient medium.

This invention further provides a method of making the complex of this invention which comprises contacting retinol-binding protein with a retinoid which binds to retinol-binding protein under conditions such that the protein and the retinoid form an intermediate complex, and contacting the intermediate complex with prealbumin under conditions that the intermediate complex and the prealbumin form a complex, wherein the concentration of retinoid in the complex is from about $2\times10^{-5}$M to about $10^{-10}$M and the concentration of prealbumin and retinol-binding protein is sufficient to maintain the retinoid concentration from about $2\times10^{-5}$M to about $10^{-10}$M, and recovering the complex.

This invention further provides a method of enhancing growth of human B cells in culture comprising growing the cells in culture in a growth medium containing a concentration of the complex of the subject invention effective to enhance growth of the human B cells.

This invention also provides a method of enhancing growth of mammalian cells in culture which comprises adding the complex of the subject invention to a synthetic tissue culture medium so as to obtain in the medium a concentration of the complex effective to enhance growth of the mammalian cells.

This invention also provides a synthetic growth medium for culturing animal cells comprising the complex of this invention at a concentration effective to enhance cell growth.

Finally, this invention provides a method of preventing the growth of human tumor cells containing growth factor which comprises removing the growth factor from the human tumor cells.

BRIEF DESCRIPTION OF THE FIGURES

FIG. 1 shows comparison between the N-terminal amino acid sequence of "aBGF" protein and human prealbumin.

The first 28 N-terminal acids of purified aBGF protein were determined in an automated Edman degradation instrument. They are identical with human prealbumin except for the portions indicated.

Figure 2:
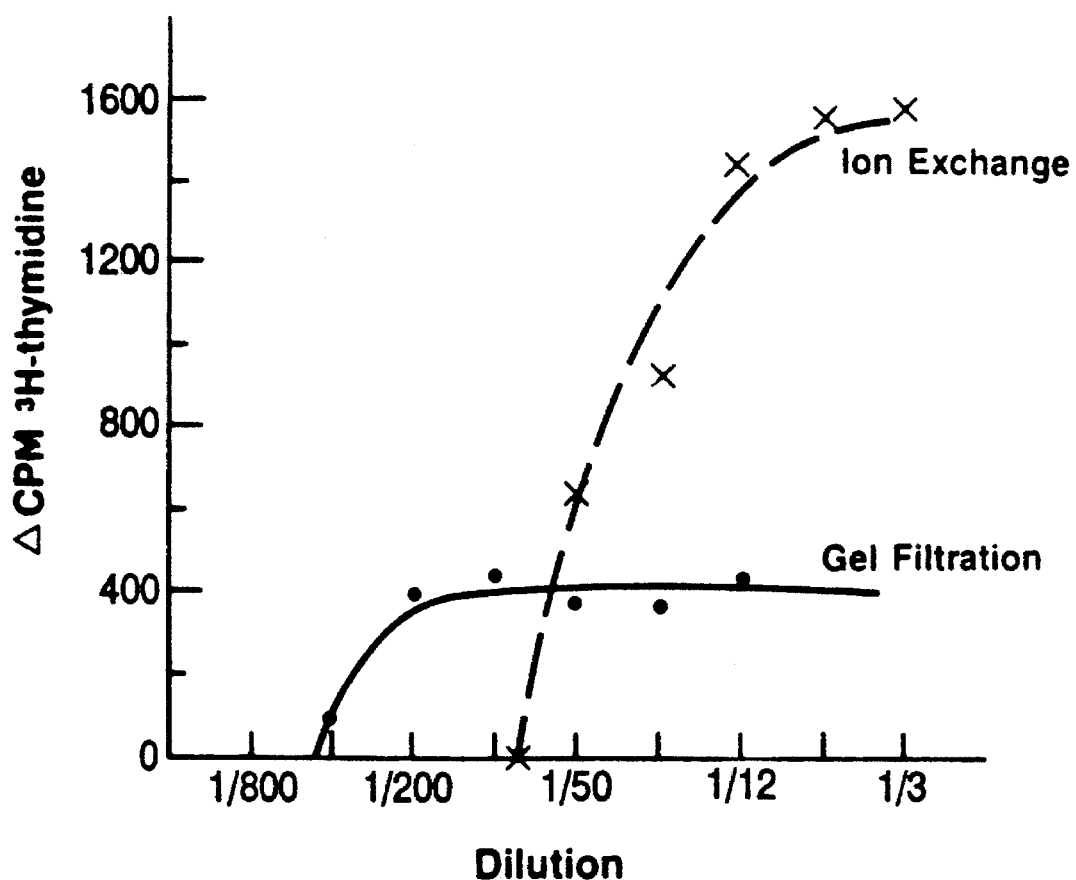

FIG. 2 shows autocrine growth factor activity after ion exchange and gel filtration chromatography.

Purification of aBGF followed the procedure given in reference 14 and outlined in the section of this application entitled "Materials and Methods". Briefly, the EBV-transformed cell line 5/2 was incubated 24 h at $6 \times 10^5$ cells/ml in serum-free medium. Proteins were concentrated from the conditioned medium by ammonium sulfate precipitation at 80% saturation, and separated by ion exchange chromatography on DE 52. Active fractions were pooled and further separated by gel filtration on AcA 54 (10). For activity assays, 5/2 target cells, washed three times with serum-free medium, were incubated at $2 \times 10^4$/ml for 72 hr in serum-free medium containing growth factor as indicated. Cells were labelled for the last 16 h with $^3$H-thymidine.

A c.p.m. expresses the differential between experimental values and the background response of $196 \pm 37$ CPM.

x=activity after ion exchange chromatography.

●=Activity after gel filtration chromatography.

Figure 3:
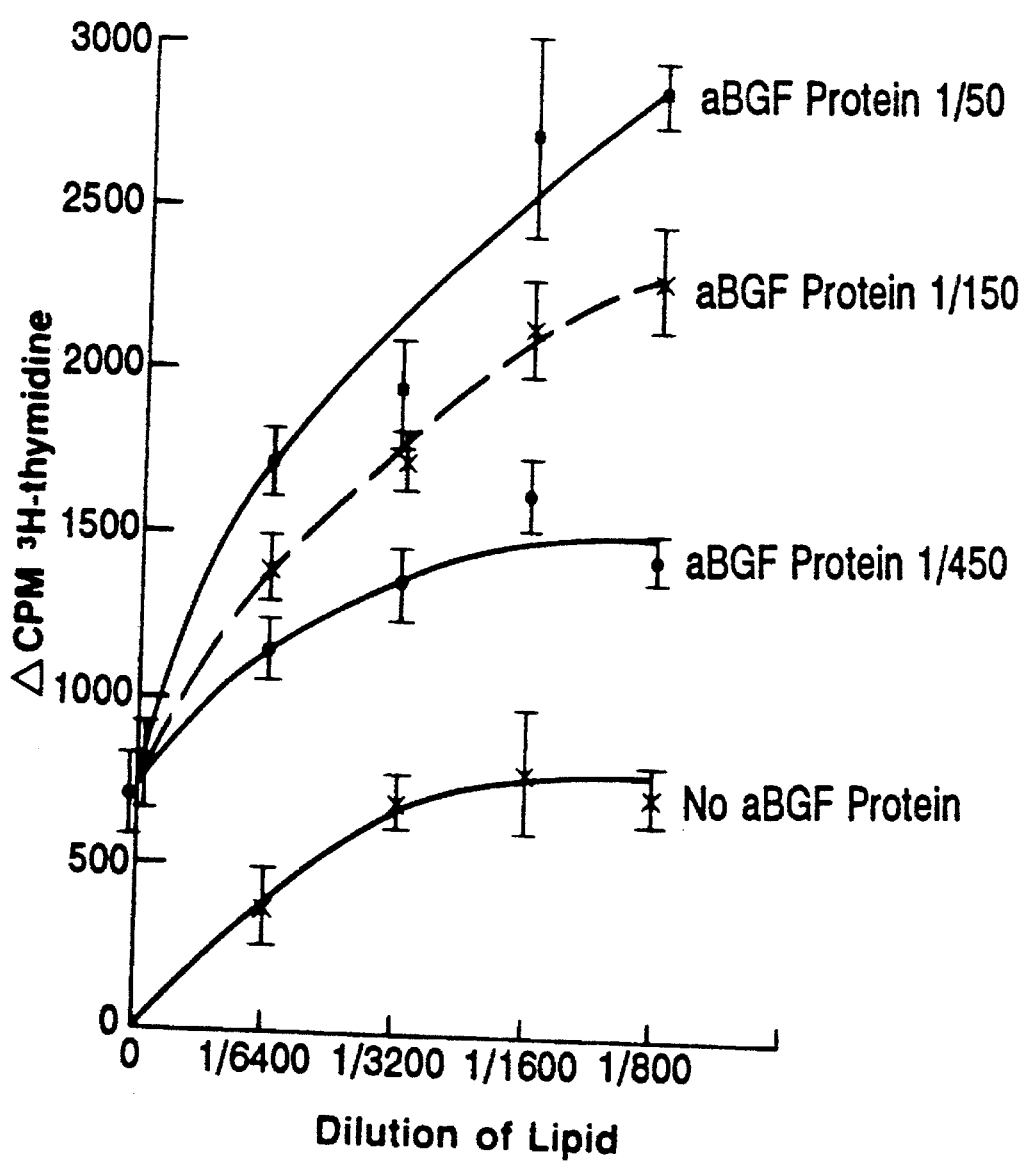

FIG. 3 shows that delipidated aBGF protein synergizes with aBGF lipid to enhance the growth of human lymphoblastoid cells.

Pooled growth-factor positive fractions obtained by ion exchange chromatography were delipidated with diethylether/ethanol 1:3 (v/v) (−20° C., overnight). Precipitated proteins were washed twice in diethylether, dried, redissolved in PBS and dialyzed extensively against PBS.

The combined ether/ethanol extracts were dried on a rotary evaporator. Lipids were dissolved in chloroform/methanol/water 10:10:1 (v/v). Aliquots of the lipid solution were evaporated to dryness and the residual lipids dispersed in serum-free medium by sonication. Dilutions of delipidated protein were mixed with different amounts of lipid. Growth factor activity was assayed as described in FIG. 1.

Figure 4:
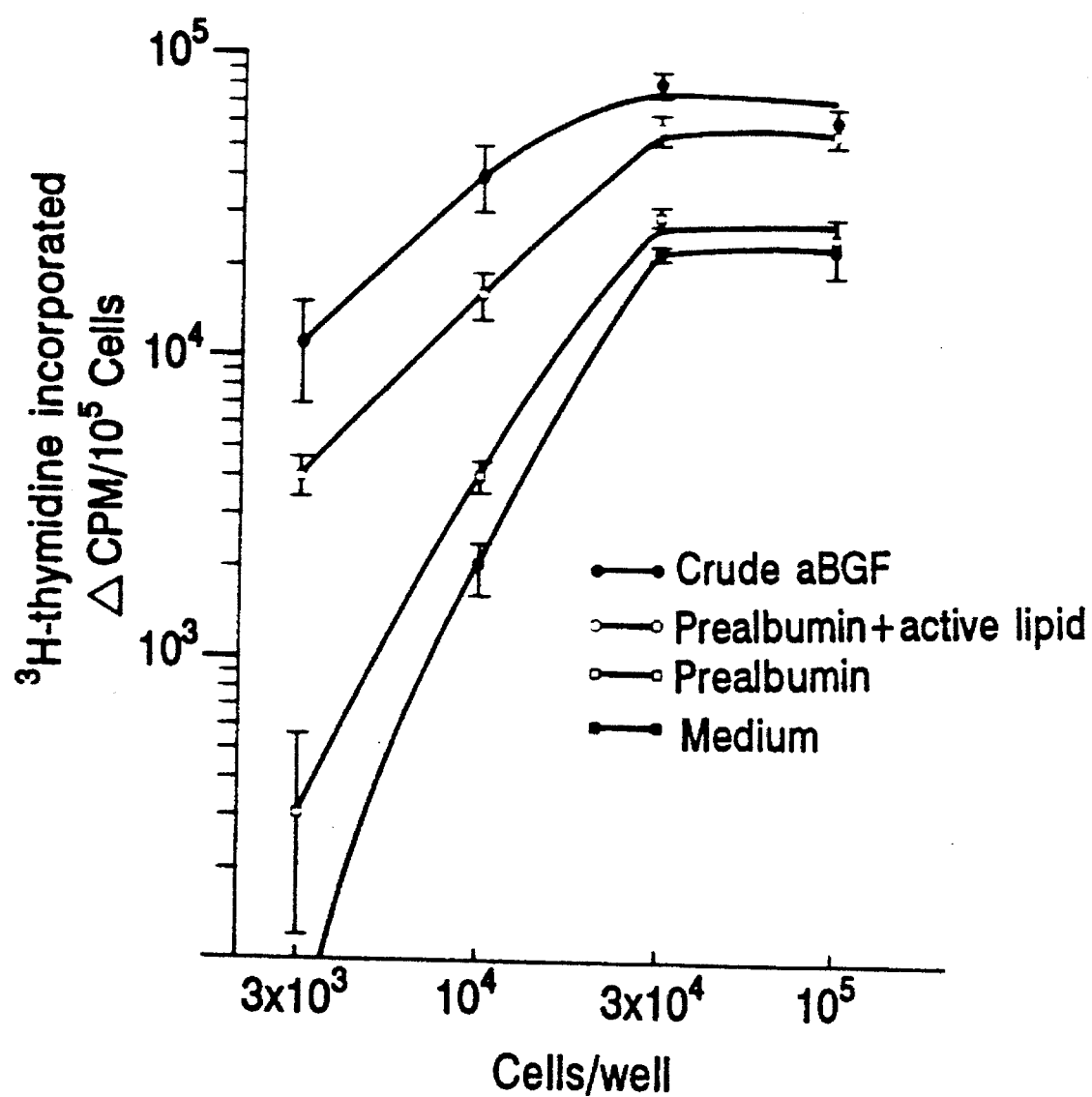

FIG. 4 shows that autocrine B cell growth factor components are effective on normal human B cells at low cell densities.

B cells were prepared from normal human spleens by Ficoll gradient centrifugation followed by treatment with OKT 4 and OKT 8 antibodies plus rabbit complement and passage through a Sephadex G-10 column. Recovered cells contained more than 90% sIg$^+$ cells.

SAC-activated B cells (500,000 cells/ml, 0.03% SAC in serum-free medium incubated for 48 hr) were washed three times and seeded at different cell concentrations in medium alone, medium containing human prealbumin, and human prealbumin plus active lipid or factor obtained by ion exchange chromatography. The cells were incubated further for 72 hours in serum-free medium and pulsed for the last 16 hours with $^3$H-thymidine. The data points represent means of triplicates entries are normalized for $10^5$ cells per culture.

Δ c.p.m. symbolizes experimental minus background counts of the scintillation counter ($114 \pm 16$ c.p.m.).

Figure 5:
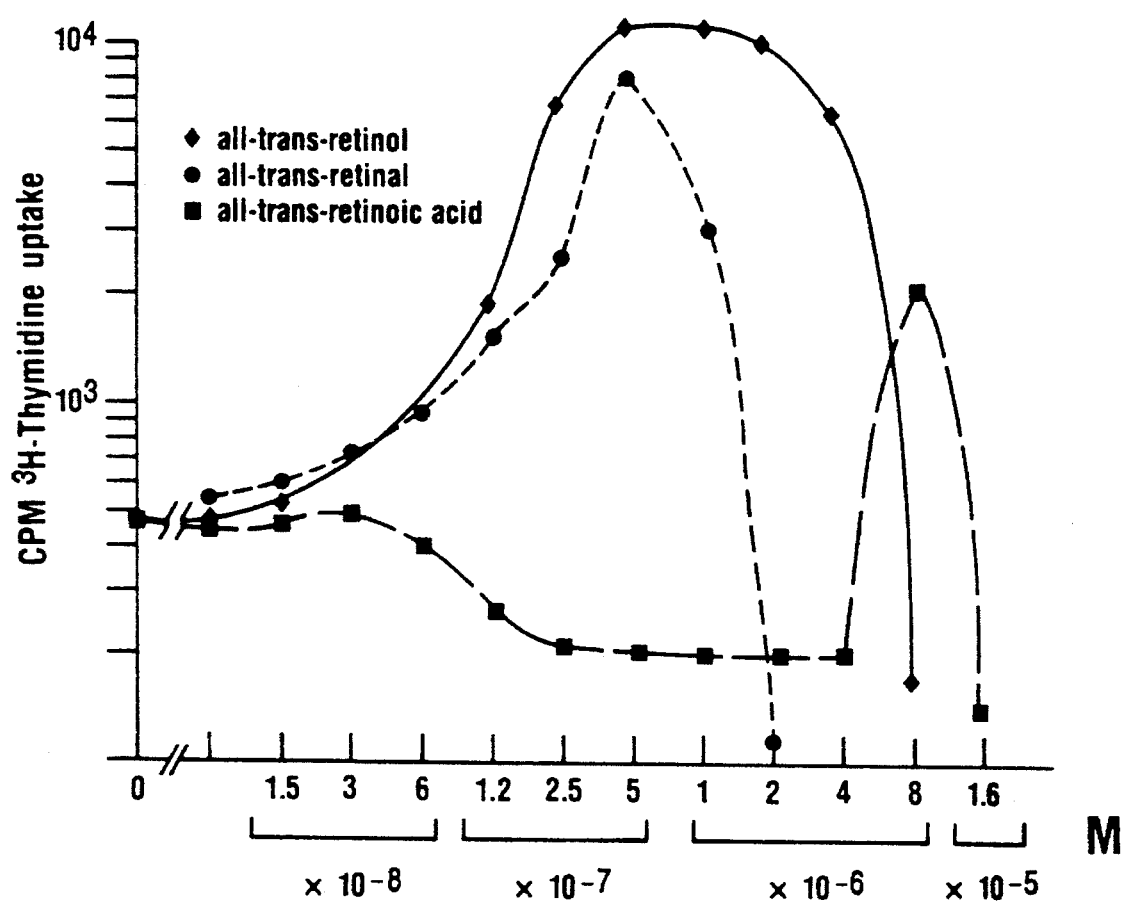

FIG. 5 shows a comparison of bioactivity between all-trans-retinol, all-trans-retinal and all-trans-retinoic acid. Bioactivity was tested on lymphoblastoid cells.

Figure 6:
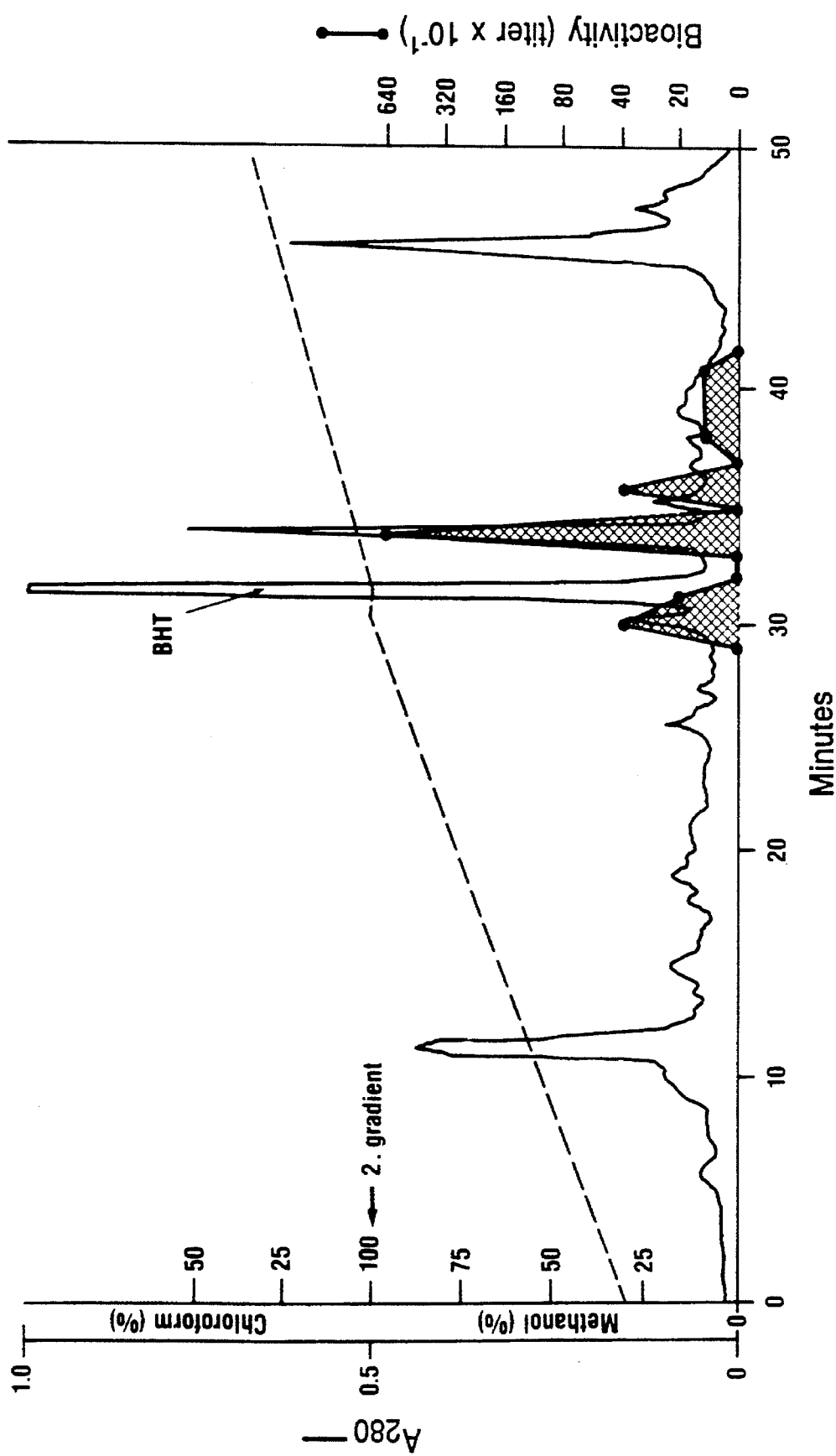

FIG. 6 shows reversed phase $C_{18}$ HPLC column chromatography. Bioactivity was tested on lymphoblastoid cells.

Figure 7A:
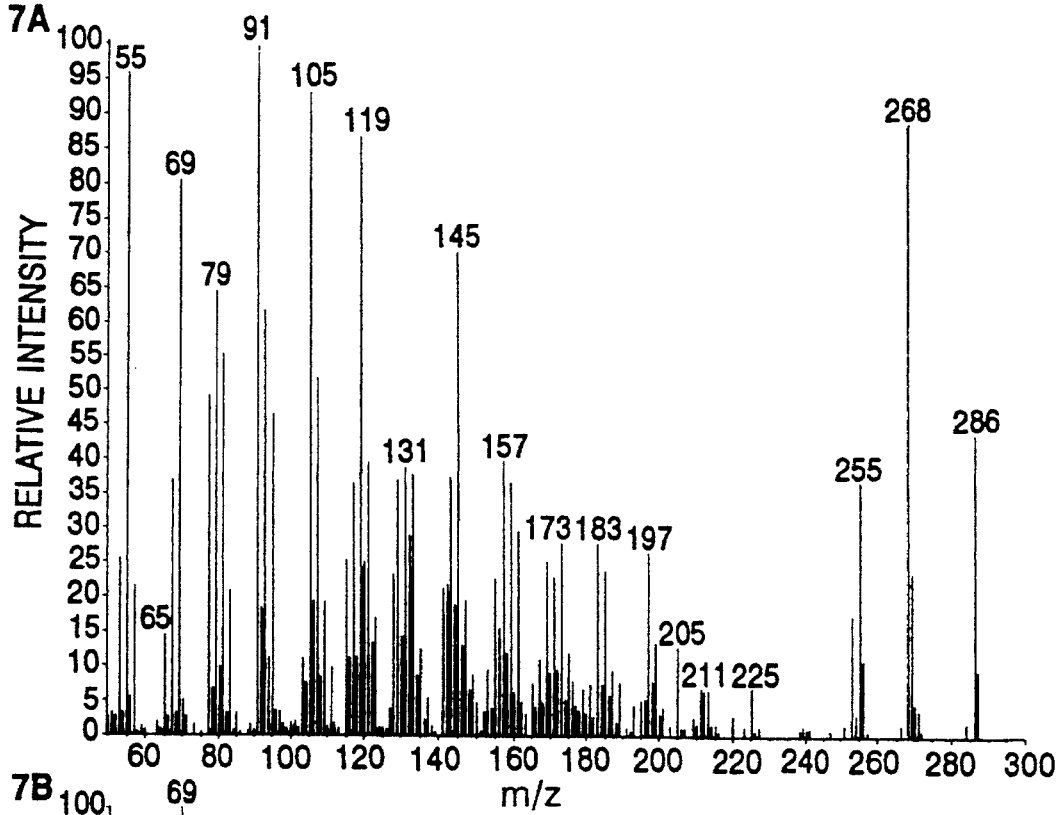

FIG. 7A shows the mass spectometry of Fraction 34 from FIG. 6. Fraction 34 was analyzed using a direct insertion probe in a V670–250 double focusing mass spectrometer.

Figure 7B:
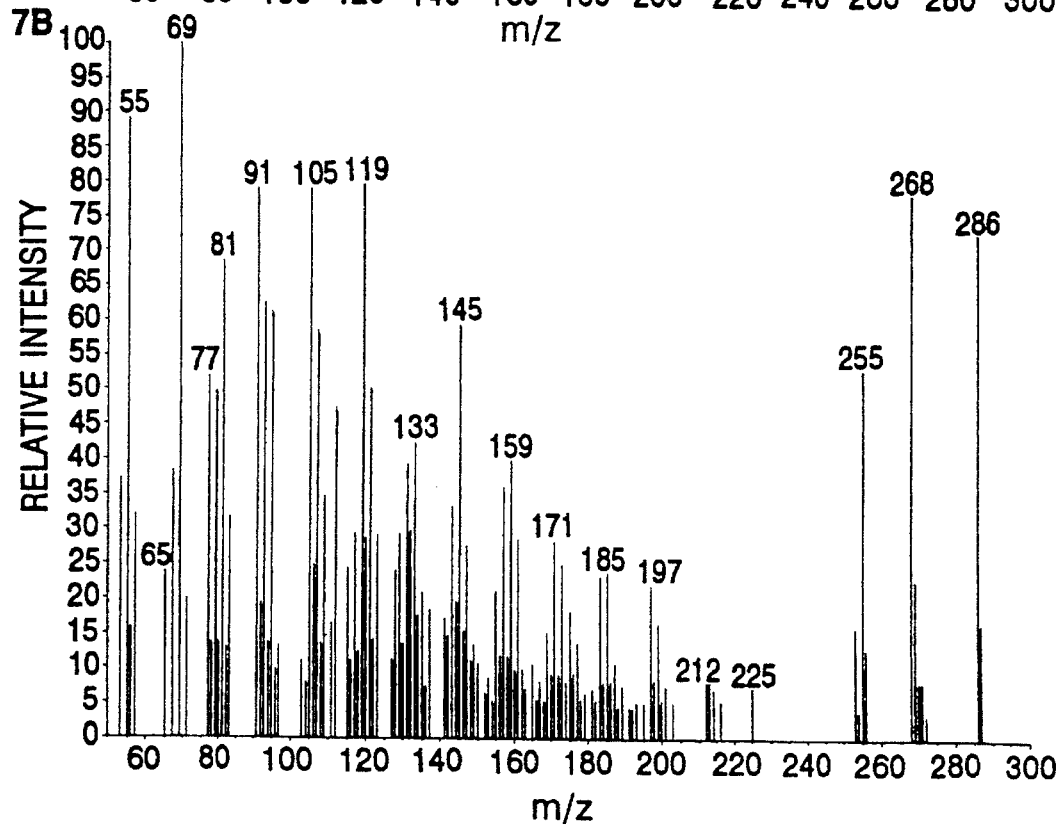

FIG. 7B shows the mass spectometry from the library reference for all-trans-retinol.

Figure 8:
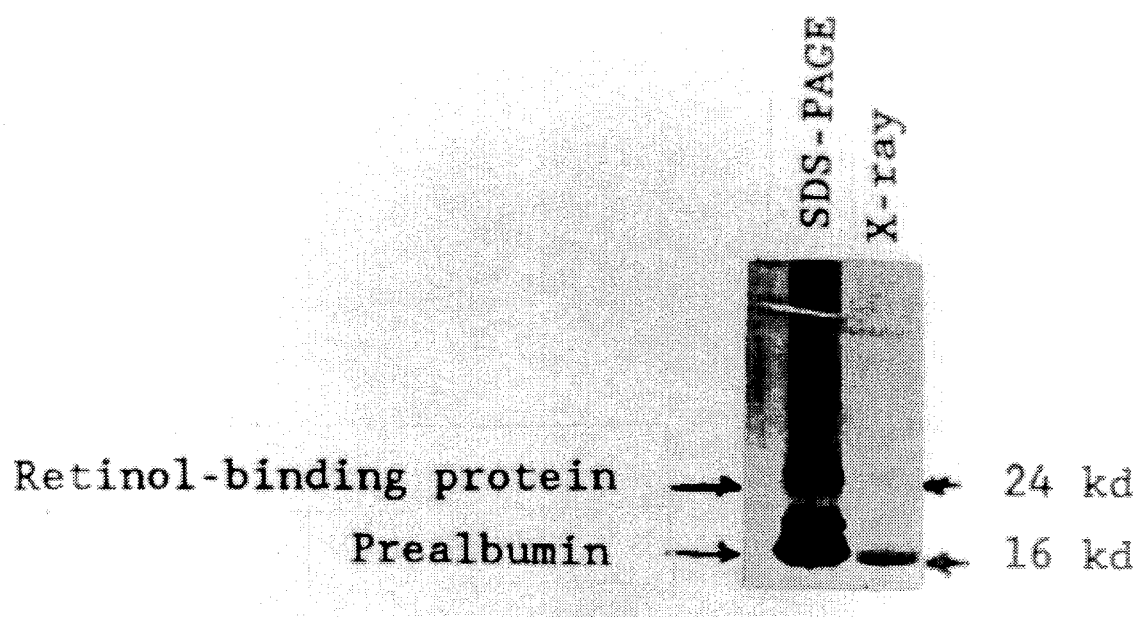

FIG. 8 shows evidence for biosynthesis of prealbumin by incorporation of $^{35}$S cysteine and $^{35}$S methionine into the prealbumin and retinol-binding protein peptide.

DETAILED DESCRIPTION OF THE INVENTION

This invention provides a complex consisting essentially of prealbumin, retinol-binding protein, and a retinoid which binds to retinol-binding protein, wherein the concentration of retinoid in the complex is from about $2 \times 10^{-5}$M to about $10^{-10}$M and the concentration of prealbumin and retinol-binding protein is sufficient to maintain the retinoid concentration from about $2 \times 10^{-5}$M to about $10^{-10}$M.

The growth factor has a narrow physiological range for activity since the individual, uncomplexed components may be toxic to cells. The prealbumin is ideally at a range from about 50 to about 200 µg/ml. The retinol-binding protein is ideally at a range from about 20 to about 40 µg/ml. The optimum ratio is equimolar amounts of each component.

In this application, the term "retinoids" includes, but is not limited to, all-trans-retinol, isomers of vitamin A such as the cis-trans isomers, derivatives of vitamin A such as retinol esters as well as the family of retinal isomers and derivatives and the family of retinoic acid, isomer and derivatives. Specific examples include all-trans-retinol, all-trans-retinal, 13-cis-retinol and 13-cis-retinal.

In one embodiment of the invention the prealbumin in the complex may be characterized as mammalian. In another embodiment, the mammalian prealbumin may be characterized as bovine or human.

This invention also provides a complex consisting essentially of retinol-binding protein and a retinoid which binds to retinol-binding protein, wherein the concentration of retinoid in the complex is from about $2 \times 10^{-5}$M to about $10^{-10}$M and the concentration of retinol-binding protein is sufficient to maintain the retinoid concentration from about $2 \times 10^{-5}$M to about $10^{-10}$M.

The present invention also provides a composition for enhancing the growth of human B cells in culture which comprises an amount of the complex of this invention effective to enhance the growth of human B cells and a nutrient medium.

The nutrient medium may be any of the standard mediums which meets the minimum biochemical requirement to sustain growth of cells. One such example includes but is not limited to a basal amino acid/salt mixture such as RPMI 1640 supplemented with insulin transferin-selenium and essential fatty acids bound to albumin. These mediums are well known in the art.

This invention also provides a composition for enhancing the growth of human B cells in culture which comprises an amount of the complex of the subject invention effective to enhance the growth of human B cells and a nutrient medium.

This invention further provides a method of making the complex of this invention which comprises contacting retinol-binding protein with a retinoid which binds to retinol-binding protein under conditions such that the protein and the retinoid form an intermediate complex, and contacting the intermediate complex with prealbumin under conditions that the intermediate complex and the prealbumin form a complex, wherein the concentration of retinoid in the complex is from about $2 \times 10^{-5}$M to about $10^{-10}$M and the concentration of prealbumin and retinol-binding protein is sufficient to maintain the retinoid concentration from about $2 \times 10^{-5}$M to about $10^{-10}$M, and recovering the complex.

The invention also provides a method of enhancing growth of human B cells in culture which comprises growing human B cells in a growth medium containing a concentration of the growth factor described hereinabove effective to enhance growth of human B cells. In one embodiment of the invention, the growth medium is a synthetic growth medium. Such types of synthetic growth media include, but are not limited to, a basal medium known in the art (e.g. RPMI 1640, insulin, transferrin and essential fatty acids)

supplemented with the complex of the subject invention at a concentration effective to enhance the growth of cells.

As noted before, the individual components of the growth factor, particularly the retinol, may be toxic if not contained within the complex. Moreover, the growth of human B cells will not be enhanced if the individual components of the growth factor are contacted with the B cells without first forming a complex. Therefore, the components of the growth factor, specifically the prealbumin, retinol-binding protein and retinoid, should be preassembled and complexed prior to contact with the B cells.

This invention also provides a method of enhancing growth of animal cells in culture which comprises adding to an synthetic tissue culture medium the complex of the subject invention so as to obtain in the medium a concentration of complex effective to enhance growth of the animal cells. In one embodiment, the cells may further be characterized as mammalian.

This invention also provides a synthetic growth medium for culturing animal cells comprising the aforementioned complex at a concentration effective to enhance cell growth. Such types of synthetic growth medium include, but are not limited to, a basal medium known in the art (e.g. RPMI 1640, insulin, transferrin and essential fatty acids) supplemented with the complex of the subject invention at a concentration effective to enhance the growth of cells.

In one embodiment of the invention, the cells may be characterized as mammalian cells. In a further embodiment, the cells may be characterized as human B cells.

The invention also provides a method of preventing the growth of human tumor cells containing growth factor which comprises removing the growth factor from the human tumor cells.

Additionally, the invention further provides a method of preventing the growth of human tumor cells containing retinoid which comprises removing the retinoid from the human tumor cells.

In one embodiment of the invention, the retinoid is all-trans-retinol.

The invention also provides a method of preventing the growth of human tumor cells containing a complex of retinoid and retinol-binding protein which comprises substituting for the retinoid in the complex a competitive inhibitor which lacks the biological activity of the retinoid and which binds to retinol-binding protein.

In one embodiment of the invention, the retinoid is all-trans-retinol.

Finally, this invention provides a method of preventing the growth of human tumor cell containing a retinoid which comprises substituting for the retinoid a competitive inhibitor which lacks the biological activity of the retinoid.

In one embodiment of the invention the retinoid is all-trans-retinol.

This invention is illustrated in the Experimental Details section which follows. This section is set forth to aid in an understanding of the invention but is not intended to, and should not be construed to, limit in any way the invention as set forth in the claims which follow thereafter.

EXPERIMENTAL DETAILS

Methods and Materials

Retinoids. All-trans-retinol, all-trans-retinal and retinoic acid were purchased from commercially-available sources. The retinoids were dissolved at a concentration of $3\times10^{-2}$M in methanol/chloroform (3:1 v/v) with $10^{-4}$M butylated hydroxy toluene (BHT) added and stored in the dark at −20° C. in a nitrogen atmosphere. Immediately before a bioassay, the stock solutions were diluted in serum-free medium.

Cells. The human EBV-transformed B LCL 5/2 was established from the peripheral blood cells of a healthy donor according to a known method (10). The cell line was grown in RPMI 1640 supplemented with 8% fetal calf serum, L-glutamine (2 mM), nonessential amino acids (10 mM), and antibiotics. The cells were tested regularly for mycoplasma infections and were consistently negative. B cells were prepared from normal human spleens by Ficoll gradient centrifugation followed by OKT4 and OKT8 treatment plus rabbit complement and passage through a Sephadex G-10 column. Recovered cells contained more than 90% $sIg^{+\ cells.}$ $5\times10^5$ cells/ml were activated either with 0.03% of fixed staphylococcus aureus Cowan stem (SAC) or 4 µg/ml of F(ab)' fragments of rabbit anti-human immunoglobulin in serum-free medium 48 h before the beginning of the experiment.

Assay for autocrine growth activity. The assay system was a modification of the assay developed by Blazar et al. (7) and Gordon et al. (8). Lymphoblastoid cells grown for 18 to 24 hr in serum-free medium at a cell density of $4\times10^5$ cells/ml or B cells activated by SAC- or anti-µ for 48 h were washed four times in RPMI 1640/0.1% fetal calf serum (FCS). The cells ($2\times10^4$/ml) were then plated in a final volume of 200 µl/well of serum-free medium in 96-well microtiter plates and grown for 72 hr in the presence of $\log_2$ dilutions of putative growth factor. Freshly prepared 5/2 cell line-conditioned medium was used as positive control. Fresh serum-free medium was the negative control. After 56 hr of culture the cells were labeled with 0.4 µCi/well of [$^3$H]thymidine (specific activity, 6.7 Ci/mmol) and 16 hr later harvested on glass fiber strips. [$^3$H] Thymidine incorporation was measured in a liquid scintillation counter. Units of autocrine B cell growth factor (aBGF) were determined according to Table 1.

Delipidation of serum protein. LPS-free fetal bovine serum and human whole blood was purchased from commercial sources. The serum or plasma was stirred overnight at −20° C. in a 100-fold volume of diethyl/ether/ethanol 1:3 (v/v). Precipitated proteins were washed twice in diethyl ether, dried, redissolved in PBS and dialyzed extensively against PBS.

Isolation of serum lipids. Human plasma or fetal bovine serum were freeze dried. All solvents had $10^{-4}$M BHT added. The dry powder was extracted twice with chloroform/methanol 2:1 (v/v) followed by two extractions with chloroform/methanol/water 10:10:1 (v/v). The combined extracts were dried on a rotary evaporator. Lipids were dissolved in chloroform/methanol/water 10:10:1 (v/v) and stored at −80° C. Immediately before a bioassay, aliquots of the lipid solution were evaporated to dryness and the residual

TABLE 1

| Dilution of RP-HPLC Fractions 23 | Proliferation of 5/2 Cells (cpm) |
| --- | --- |
| 1/50 | 1320 |
| 1/100 | 1170 |
| 1/200 | 1280 |
| 1/400 | 910 |
| 1/800 | 290 |

TABLE 1-continued

| Dilution of RP-HPLC Fractions 23 | Proliferation of 5/2 Cells (cpm) |
|---|---|
| HB 101 | 330 |

One unit was defined as the reciprocal of the dilution of aBGF, which shows full activity in the aBGF assay. Therefore Fraction 23 corresponds to 200 µ/ml.
The aBGF activity was determined with the assay for autocrine growth activity described in Materials and Methods.

lipids dispersed in serum-free medium by sonication.

Lipid separation on a reversed-phase HPLC column. The crude lipid mixture was loaded on a semipreparative reversed-phase $C_{18}$ HPLC column. Lipids were eluted with a linear gradient of water/methanol/chloroform. The gradient started with water/methanol 70:30 (v/v), went in 30' to 100% methanol and in another 30' to methanol/chloroform 50:50 (v/v). The flow rate was 3 ml/min.

Mass spectroscopy. Bioactive lipids were analyzed using a direct insertion probe in a V670-250 double focusing mass spectrometer.

Isolation of retinol-retinol binding protein complex. 40 mg of human prealbumin were covalently bound to 3 ml of CNBr activated sepharose. 50 ml of human plasma were passed through the column. The column was washed with 30 ml of 0.04M Tris HCl (pH 7.4)/0.5M NaCl and eluted with 1 ml fractions of distilled water. Purity was established by SDS-PAGE with silver stain and the optical densities at 280 nm and 340 nm were determined.

Assay for IL 1 activity. IL 1 activity was assessed in the lymphocyte activation factor assay (11), which we modified slightly by using 0.5% human serum instead of FCS. Recombinant human IL 1-α was used as reference standard.

Assay for tumor necrosis factor (TNF) activity. TNF activity was measured on TNF-sensitive L(M) cells (12) in 96-well microtiter plates with 1.0 µµ/ml of actinomycin D added. TNF-resistant L(M) cells were used to exclude nonspecific toxicity. The cells were pulsed after 24 hr with 0.4Ci/well of [$^3$H]thymidine for 4 hr.

Assay for IL 2 activity. IL 2 was assayed by using the IL 2-dependent murine cytotoxic T cell line 1 (13).

Preparation of 5/2 cell line-conditioned medium. Cells were taken from their exponential phase of growth, washed once, and reseeded at $4 \times 10^5$ cells/ml in serum-free HB 101 medium. After 24 hr, conditioned medium was cleared of cells by centrifugation, passed through a 0.22-µm filter, and used immediately for the purification of growth factor.

Ammonium sulfate precipitation. $(NH_4)_2SO_4$ (1683 g) was added to 3 liters of 5/2 cell line-conditioned medium to achieve 80% saturation. After gentle stirring overnight at 4° C., the precipitate was spun down (10,000 ×G. 30 min), dissolved in 0.05 M Tris-HCl, pH 7.8, in a final volume of 135 ml, and subsequently dialyzed against 50 volumes of 0.5 M Tris-HCl buffer, pH 7.8 for hr with five changes of the dialyzing buffer.

Anion exchange chromatography (DEAE-cellulose). The dialyzed concentrate was loaded on 250-ml column of DEAE-cellulose, equilibrated with 0.05 M Tris-HCl, pH 7.8. Bound proteins were eluted with a stepwise gradient of Tris-buffered NaCl: 0.075 M NaCl (150 ml), 0.125 M NaCl (250 ml), 0.175 M NaCl (250 ml), and 0.300 m NaCl (250 ml). Fraction size was 25 ml. Fractions containing growth factors were pooled and concentrated by dialyzing against phosphate-buffered saline (PBS), pH 7.2, containing polyethyleneglycol (relative molecular mass ($M_r$) 6000) (polyethyleneglycol 6000; 50% w/v).

Gel filtration. The concentration DEAE-cellulose preparation (18 ml) was applied to an AcA 54 Ultrogel column (2.6×90 cm), equilibrated with PBS. The flow rate was adjusted to 38 ml/hr and 7.5-ml fractions were collected. The column had been calibrated with m.w. markers: bovine serum albumin ($M_r$ 68,000), chymotrypsinogen ($M_r$ 25,700), and ribonuclease A ($M_r$ 14,300), all commerically obtained.

Reversed-phase high performance liquid chromatography (RP-HPLC). The separation was performed on a $C_{18}$ column. Buffer A was 100 mM $CH_3COONH_4$ pH 4.0 and buffer B was buffer A in 50% 1-propanol. The pool containing growth activity obtained from gel filtration was acidified with acetic acid to pH 4.0 and loaded onto the $C_{18}$ column without regard to sample volume. The column was washed with buffer A (20 min), and bound proteins were eluted by using a steep gradient of 0 to 40% buffer B within the first 20 min and a 40 to 100% gradient of buffer B in 120 min. The percentage of buffer A was inversely proportional to buffer B. The flow rate was adjusted to 1 ml/min and 3-ml fractions were collected.

Isoelectric focusing (IEF). One milliliter of purified aBGF was supplemented with 20% glycerol (v/v) and 2% ampholine (v/v) at pH 3.5 to 10. A 5 to 60% glycerol density gradient containing 2% ampholine (pH 3.5 to 100) was layered into an IEF column. The sample was applied onto the isodense region of the gradient, followed by IEF (2000 V, 24 hr, 4° C.). Five-milliliter fractions were collected and the pH was determined in each fraction. The fractions were dialyzed against HB 101 and then tested for growth activity. NaDodSO$_4$/polyacrylamide gel electrophoresis NaDodSO$_4$/-PAGE). The discontinuous Tris/glycine system of Laemmli (14) was used for 1.5-mm slab gels of 15% acrylamide. The samples (lyophilized protein eluted from HPLC) were treated with 1% NaDodSO$_4$ 0.0625 M Tris-HCL (pH 6.8) at 37° C. for 1 hr under both reducing (5% 2-mercaptoethanol) and nonreducing conditions and then loaded on the gel. After electrophoresis, gels were stained by the silver-staining method. Apparent m.w. lactoglobulin ($M_r$ 18,400), lysozyme ($M_r$ 14,300), and were determined by using protein standards: ovalbumin ($M_r$ 43,000), chymotrypsinogen ($M_r$ 25,700), β-lactoglobulin ($M_r$ 18,400), lysozyme ($M_r$ 14,300), and cytochrome c ($M_r$ 12,300). After electrophoresis under nonreducing conditions, parallel gels were sliced in 2-mm sections, and proteins from each slice were eluted into $P_i$/NaCl. The eluted material was assayed for growth-stimulatory activity.

Protein assay. The protein content of samples was measured by absorption at 280 nm. For protein concentrations of <2 µg/ml, samples were subjected to NaDodSO$_4$/PAGE; the protein bands were visualized by the silver-staining technique, and the protein concentration was estimated by comparison with a serial dilution of known amounts of proteins.

Autoradiography. Lymphoblastoid cells were labelled with $^{35}$S cysteine and $^{35}$S methionine. The supernatant was precipitated with ammonium sulfate. The prealbumin/retinol-binding protein complex was separated with an affinity column. The proteins were separated by a SDS PAGE gel with silver staining.

Results

Immune activity and homeostasis of B cells are governed by a complex network of growth and differentiational signals. Research so far has emphasized the role of proteins and glycoproteins as B cell regulators. The present inventors now have evidence that B cell-produced lipids also may participate in B cell homeostasis and that bioactive lipid molecules may use serum proteins as carriers. In attempting to study and analyze a previously described B cell-derived B cell growth factor (10), a lipid-protein complex with novel biological properties has been found. This complex occurs in serum and in the culture fluids of EBV-transformed human B lymphocytes and of activated normal human B cells. The protein moieties of the complex are prealbumin and retinol-binding protein. The lipid moiety of the complex comprises all-trans-retinol, commonly known as vitamin A, or derivatives of vitamin A.

Human B cells transformed by Epstein-Barr virus grow in defined serum-free medium at high cell density (>100,000 cells/ml). However, when removed from high cell density serum-free conditions after one day, washed in serum-free medium and reseeded in fresh serum-free medium at low density, the growth rate decreases drastically and most of the cells die. Suitable growth conditions are restored by the addition of fetal bovine or human serum (Table 2).

A factor released by EBV-transformed B cells, provisionally termed "autocrine B cell growth factor" (aBGF) (10), was purified by a four-step procedure, namely ammonium sulfate precipitation, ion exchange chromatography,

TABLE 2

Comparison of growth-stimulating effect between serum, delipidated serum proteins and serum lipids.

|  | ΔCPM |
| --- | --- |
| Serum-free medium | 1,952 ± 138 |
| Human serum | 16,896 ± 232 |
| Delipidated serum proteins | 4,094 ± 772 |
| Serum lipid | 4,360 ± 266 |
| Protein + lipid | 13,211 ± 721 |

Washed 5/2 cells (1,500/well) were incubated for 72 h in serum-free medium. DNA synthesis was assessed as described. The experiment was done in triplicate.
Protein and lipid concentrations correspond to 3% serum.

gel filtration and reversed phase HPLC. B cell stimulatory activity was monitored by an assay devised by Blazar, et al. (7). A 16 kD protein was isolated which formed dimers and tetramers. Since its 28 N-terminal amino acid sequence corresponds to the bovine prealbumin sequence at 15 of 16 residues, and since there is 82% homology to human prealbumin, it appears likely that the 16 kD protein constitutes the monomeric subunit of bovine prealbumin (FIG. 1). Prealbumin is a stable tetrameric serum protein consisting of four identical subunits (11). The full physiological functions of prealbumin are unknown, except for evidence that it acts as a carrier for thyroxine and of vitamin A via retinal-binding protein. The subunits are so arranged as to form a central channel containing two binding sites for thyroxine (12–14).

In the course of aBGF purification it was noted that activity was retained through the ion-exchange chromatography, but was lost during the subsequent gel filtration step. This decrease in activity occurred despite a nearly ten-fold titrated enrichment of specific protein. The ion-exchange material yielded six-fold to ten-fold increases in $^3$H-thymidine uptake in cultures of EBV-transformed target cells, while the relative increase elicited by the gel filtration material was merely two-fold (see FIG. 2). These findings prompted the current inventors to search for a cofactor that might act in concert with the protein and which was lost during gel filtration. Back-mixing of fractions failed to restore the high proliferation index, suggesting that the postulated cofactor was absent from other fractions generated by gel filtration chromatography and possibly remained absorbed to the gel-filtration matrix. Since the protein copurifying with activity was prealbumin, and prealbumin is known to function as a carrier for thyroxine and vitamin A, it was envisaged that a similar molecule of small molecular weight might act as a cofactor for aBGF. Although thyroxine itself did not act in such a fashion, a cofactor was found in chloroform/methanol or ether/ethanol extracts of crude active ion-exchange chromatography fractions of aBGF, but not in elutes from the gel filtration beads. Because of its solubility in organic solvents, it was hypothesized that the costimulatory factor was a lipid. Ion exchange material extracted with an ether/ethanol mixture yielded a delipidated protein with mild stimulatory capacity (two-fold over background), not unlike the material obtained after gel filtration. Lipid from the ether/ethanol phase showed similar low stimulatory activity, but the combination of delipidated protein and lipid restored biological activity to the high level (10-fold) obtained with the crude ion exchange fractions. Furthermore, both lipid and protein concentrations affected the level of reconstituted activity (FIG. 3). When human prealbumin was substituted for the delipidated protein, it synergized with lipid extract in a manner similar to aBGF protein (see Table 3).

Serum lipids were isolated from human serum by solvent extraction with diethylether/ethanol or chloroform/methanol/water mixtures. Delipidated proteins were the residue after ether/ethanol extraction. The growth stimulatory effects of lipids and delipidated proteins for EBV-transformed cells were tested either alone or in combination. The results of Table 2 show definite, but modest increases in $^3$H-thymidine

TABLE 3

| | Lipid (1/1,500) | |
| --- | --- | --- |
| | Without Δ c.p.m. | With Δ c.p.m. |
| Serum-free medium | 0* | 463 |
| Human Prealbumin | | |
| 5.0 ng/ml | 244 | 1,098 |
| 0.5 ng/ml | 282 | 1,375 |
| "aBGF" protein | | |
| 2 ng/ml | 156 | 1,016 |
| 1 ng/ml | 201 | 1,091 |

Washed 5/2 target cells were cultured in triplicate at $10^4$ cells/ml for 72 h under conditions indicated. $^3$H-thymidine (0.4 μCi/well) was added for the last 16 h. Results are recorded as the average of triplicate cultures. The standard deviations were less than 20%.
Δ c.p.m. expresses the differential between total c.p.m. and the background response (156 ± 28).
*Microscopic inspection showed all cells to be dead.

uptake by either compound alone, but when mixed, a synergistic effect occurred which nearly matched the growth stimulation potential of whole serum.

The growth-promoting properties of the lipid extract on normal human B cells was examined. In the experiment shown in FIG. 4, staphylococcus aureus (SAC) activated human B lymphoblasts gave a significant proliferative response to the lipid/prealbumin combination and to the crude aBGF ion exchange preparation, particularly at low cell density. Activated, but not resting normal B cells, also produce an equivalent lipid cofactor. Solvent extraction of medium conditioned by B cells stimulated with SAC (0.02%) or anti-μ (10 μg/ml) yielded a stimulatory activity indistinguishable from that derived from EBV-transformed cells.

FIG. 5 shows a comparison of bioactivity between all-trans-retinol, all-trans-retinal and all-trans-retinoic acid. Bioactivity was tested on lymphoblastoid cells.

The culture medium may also be synthetic, comprising a basal medium known in the art (e.g. RPMI 1640, insulin, transferrin and essential fatty acids) supplemented with the complex at a concentration effective to enhance the growth of cells.

Crude lipid activity was resistant to saponification with 4M potassium hydroxide for two hours at 37° C. but was not stable over prolonged periods of time in aqueous solution at 4° C. and was destroyed by ultraviolet light. The bioactivity decayed within hours at room temperature but decay could be slowed by the addition of the antioxidant butylated hydroxy toluene (BHT) and by storage of the sample in the dark at −80° C. in a nitrogen atmosphere. The lipid mixture was chromatographed on a reversed phase $C_{18}$ HPLC column (FIG. 6) with a linear water/methanol/chloroform gradient and 89% of total bioactivity had been eluted at minute 34. Corresponding to the main bioactivity was an optical absorption peak registering at the wavelengths of 280 nm and 340 nm. The material collected in this fraction fluoresced when exposed to UV light. The low resolution mass spectrum is given in FIG. 7A which shows a m/z of 286 for the molecular ion, and masses of 268, 255 and 253 respectively for the first breakdown products. A library computer search showed high homology of the observed spectrum with the reference spectrum of all-trans-retinol (FIG. 7B). Accordingly, authentic all-trans-retinol has been tested and a growth-enhancing effect on activated human B cells has been found similar in magnitude to the ones elicited by bioactive HPLC fraction 34 and the crude serum lipid (Table 4).

Further evidence for identity of the bioactive HPLC fraction 34 with all-trans-retinol was obtained by chromatographic comparisons which yielded identical profiles on a HPLC $C_{18}$ column and by thin layer chromatography including, in the latter method, similar bands of breakdown products.

A second group of compounds with low-titered bioactivity was observed in HPLC fractions 38 to 41, and these were identified as retinyl esters by mass spectrometry. In addition, fractions 30 and 36 contained bioactivity. Repeat experiments with fetal bovine serum gave similar compounds and bioactivities.

TABLE 4

Comparison between the growth-stimulating effect of human serum, retinol and purified lipid activity on activated human B cell blasts.
Δ CPM

|  | SAC-blasts (2,000/well) | anti-μ blasts (2,000/well) | EBV-blasts (1,500/well) |
|---|---|---|---|
| 0 | 515 ± 53 | 383 ± 48 | 1,451 ± 366 |
| 3% human serum | 1,780 ± 230 | n.d.* | 10,446 ± 1,021 |
| Fraction 34 (1/5000) | 2,819 ± 337 | 4,783 ± 841 | 6,136 ± 213 |
| Retinol ($3 \times 10^7$ M) | 3,091 ± 421 | 4,375 ± 546 | 6,910 ± 1,015 |

Washed B cell blasts were incubated for 72 h in serum-free medium. DNA synthesis was assessed as described. The experiment was done in triplicate.
*not done.

In serum, the natural carrier of retinol is retinol binding protein (RBP) complexed with prealbumin (PA). The trimeric complex is stable under isotonic conditions but dissociation of the two proteins occurs in distilled water. Retinol is retained by RBP. To test for the involvement of the natural carrier system, RBP was isolated by use of a solid-phase PA column consisting of human PA attached to CNBr activated Sepharose. Fresh human serum was passed through the affinity column and bound proteins were eluted with water. The eluted proteins by SDS PAGE proved to be 70% RBP, with some PA contamination and, according to their optical absorption ratio, at 280 and 340 nm of 0.7 contained retinol at approximately 80% saturation. When assayed in cultures of lymphoblastoid cells, the RBP-retinol complex showed growth-enhancing activity similar in magnitude to activities of crude serum lipids and of commercially available retinol. When the RBP-retinol complex was extracted with methanol/chloroform and the extract subjected to HPLC on a $C_{18}$ column, a single activity peak emerged in fraction 34, the same fraction where authentic all-trans-retinol is eluted.

As shown by autoradiography, activated human B cells produce retinol-binding protein and prealbumin and release into the medium (FIG. 8).

Dose-response curves establish that all-trans-retinol, tested in serum-free medium in the presence of RBP/PA, is optimally active at a concentration of $2 \times 10^{-6}$ to $5 \times 10^{-7}$ M, a range corresponding to the physiological concentration in serum ($10^{-6}$ M retinol). At concentrations above 8 retinol is toxic to human B cells in serum-free, as well as in 7% serum-supplemented medium. All-trans-retinal is comparable in bioactivity at a range of $10^{-7}$ to $5 \times 10^{-7}$ molar, but at $2 \times 10^{-6}$ M displays toxicity. Retinoic acid, commonly assumed to be the most active retinol derivative in cell culture, has marginal bioactivity on B cells at $10^{-5}$ (15 to 25% growth-enhancing capacity as compared to retinol) and is toxic at higher doses. At concentrations of $4 \times 10^{-6}$ M to $6 \times 10^{-8}$ M there is a noticeable suppression of thymidine incorporation. Mixtures of retinol and retinoic acid at appropriate concentrations are growth stimulatory. Retinoic acid has not been found in fresh serum at concentrations above $10^{-8}$ M.

The results reported here support the contention that human B cells are subject to control by autocrine growth factors (10), and that this growth factor comprises prealbumin, and retinoids.

REFERENCES

1. Delarco, and Todaro, G., Proc. Nat. Acad. Sci. USA 75, 4001 (1978).

2. Kaighn, M. E., Kirk, D., Szalay, M., and Lechner, J., Proc. Nat. Acad. Sci. USA 78, 5673 (1981).

3. Uittenbogaart, C. H., and Fahey, J. L., Proc., Nat. Acad. Sci. USA 79, 7004 (1982).

4. Miller, G., Welte, K., Holloway, K., Moore, M. A. S., and Mertelsmann, R., Leukemia: Recent Advances in Biology and Treatment, 303–312 (1985).

5. Cuttitta, F., Carney, D. N., Mulshine, J., Moody, T. W., Fedorko, J., Fischler, A., and Minna, J. D., Nature 316, 823 (1985).

6. Welte, K., and Mertelsmann, R., Cancer Invest. 3, 35 (1985).

7. Blazer, B. A., Sutton, L. M., and Strome, M., Cancer Res. 43, 4562 (1983).

8. Gordon, J., Ley, S. C., Melamed, M. D., Aman, P., and Hughes-Jones, N. C., J. Exp. Med. 159, 1554 (1984).

9. Gordon, J., Ley, S. C., Melamed, M. D., Aman, P., and Hughes-Jones, N. C., Nature 310, 145 (1984).

10. Buck, J., Hammerling, U., Hoffmann, M. K., Levi, E., and Welte, K., J. Immunol. 138, 2923–2928 (1987).

11. Rask, L., Peterson, P. A., and Nilson, S. F. J. Biol. Chem. 246, 6087–6097 (1971).

12. Kanda, Y., Goodman, D. S., Canfield, R. E., and Morgan, F. J., *J. Biol. Chem.* 249, 6796–6805 (1974).

13. Blake, C. C. F., Geisow, M. J., and Oatley, S. J. *J. Mol. Biol.* 121, 339–356 (1978).

14. Blake, C. C. F., and Oatley, S. J. Nature 268, 115–120 (1977).

15. Cuthbert, J. A., and Lipsky, P. E. *J. Biol. Chem.* 261, 3620–3627 (1986).

16. Arai, S., Yamane, I., Tanno, Y., and Takishima, T., Proc. Soc. Exp. Biol. Med. 159, 444–448 (1977).

17. Swendeman, S. and Thorley-Lawson, D. A., Embo J. 6, 1637–1642 (1987).

What is claimed is:

1. A growth medium comprising a complex at a concentration effective to enhance B cell growth, the complex consisting essentially of prealbumin, retinol-binding protein, and a retinoid which binds to retinol-binding protein, wherein the concentration of retinoid in the complex is from $2 \times 10^{-5}$ M to $10^{-5}$ M and the concentration of prealbumin and retinol-binding protein is sufficient to maintain the retinoid concentration from $2 \times 10^{-5}$ M to $10^{-10}$ M.

2. A method of enhancing the growth of B cells in culture which comprises culturing the B cells in the growth medium of claim 1.

3. The method of claim 2, wherein the B cells are human B cells.

4. The growth medium of claim 1, wherein the molar ratio of prealbumin, retinol-binding protein, and retinoid is about 1:1:1.

5. The growth medium of claim 1, wherein the retinoid is all-trans-retinol.

6. The growth medium of claim 1, wherein the retinoid is all-trans-retinal.

7. The growth medium of claim 1, wherein the retinoid is 13-cis-retinol.

8. The growth medium of claim 1, wherein the retinoid is 13-cis-retinal.

9. The growth medium of claim 1, wherein the prealbumin is mammal prealbumin.

10. The growth medium of claim 9, wherein the mammal prealbumin is human prealbumin.

11. The growth medium of claim 9, wherein the mammal prealbumin is bovine prealbumin.

* * * * *